(12) United States Patent
Kikuchi (10) Patent No.: US 11,627,886 B2
(45) Date of Patent: Apr. 18, 2023

(54) BLOOD PRESSURE MEASURING APPARATUS

(71) Applicant: NIHON KOHDEN CORPORATION, Tokyo (JP)

(72) Inventor: Yoshiharu Kikuchi, Tokorozawa (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 44 days.

(21) Appl. No.: 16/497,603

(22) PCT Filed: Mar. 20, 2018

(86) PCT No.: PCT/JP2018/011062
§ 371 (c)(1),
(2) Date: Sep. 25, 2019

(87) PCT Pub. No.: WO2018/180783
PCT Pub. Date: Oct. 4, 2018

(65) Prior Publication Data
US 2020/0029824 A1    Jan. 30, 2020

(30) Foreign Application Priority Data
Mar. 29, 2017    (JP) .............................. JP2017-065003

(51) Int. Cl.
*A61B 5/022*    (2006.01)
*A61B 5/00*    (2006.01)

(52) U.S. Cl.
CPC ............ *A61B 5/022* (2013.01); *A61B 5/6843* (2013.01); *A61B 5/7239* (2013.01)

(58) Field of Classification Search
None
See application file for complete search history.

(56) References Cited

U.S. PATENT DOCUMENTS

2004/0138538 A1    7/2004    Stetson
2005/0283086 A1    12/2005   Satoh et al.
(Continued)

FOREIGN PATENT DOCUMENTS

CN    102198001 A    9/2011
CN    106231995 A    12/2016
(Continued)

OTHER PUBLICATIONS

Office action issued in Patent Application No. 2017-065003 dated Nov. 17, 2020.
(Continued)

*Primary Examiner* — Christian Jang
(74) *Attorney, Agent, or Firm* — Pearne & Gordon, LLP (57) ABSTRACT

A blood pressure measuring apparatus for measuring blood pressure of a subject using a cuff attached to the subject includes a processor and a memory to store instructions that are readable by the processor. As the instructions are executed by the processor, the apparatus generates a pulsation signal of the subject while increasing an inner pressure of the cuff; generates a first-order differential signal by differentiating the pulsation signal. The apparatus then detects an inappropriate attachment state of the cuff based on at least one of: a bottom value of the first-order differential signal; a relationship between a peak value and the bottom value of the first-order differential signal; an amplitude amount of the first-order differential signal including the bottom value in a unit time; and a relationship between the amplitude amount and an amplitude amount of the first-order differential signal including the peak value in a unit time.

6 Claims, 6 Drawing Sheets

(56) References Cited

U.S. PATENT DOCUMENTS

| | | | |
|---|---|---|---|
| 2011/0054330 A1 | 3/2011 | Pfeiffer et al. | |
| 2013/0030310 A1* | 1/2013 | Sawanoi et al. | |
| 2016/0242672 A1* | 8/2016 | Mikoshiba | A61B 5/24 |
| 2016/0278645 A1 | 9/2016 | Yoon | |
| 2017/0027459 A1* | 2/2017 | Shimuta | A61B 5/02438 |
| 2019/0365255 A1 | 12/2019 | Kitagawa et al. | |

FOREIGN PATENT DOCUMENTS

| | | |
|---|---|---|
| EP | 2 572 633 A2 | 3/2013 |
| JP | 2001-008907 A | 1/2001 |
| JP | 2001-204695 A | 7/2001 |
| JP | 2002-078685 A | 3/2002 |
| JP | 2006-263354 A | 10/2006 |
| JP | 2011-229736 A | 11/2011 |
| WO | 2011-105195 A1 | 1/2011 |
| WO | 2011-122125 A1 | 10/2011 |
| WO | 2014-124086 A1 | 8/2014 |
| WO | 2018-168792 A1 | 9/2018 |

OTHER PUBLICATIONS

International Search Report Issued in Patent Application No. PCT/JP2018/011062 dated Jun. 7, 2018.
Written Opinion Issued in Patent Application No. PCT/JP2018/011062 dated Jun. 7, 2018.
Chinese Office Action dated Feb. 1, 2023 issued in Patent Application No. 201880023076.2.

\* cited by examiner

BLOOD PRESSURE MEASURING APPARATUS

TECHNICAL FIELD

The present disclosure relates to a blood pressure measuring apparatus for measuring a blood pressure of a subject using a cuff attached to the subject.

BACKGROUND ART

Japanese Patent Publication No. 2002-078685A discloses what is called an inflation blood pressure measuring apparatus for determining a systolic blood pressure etc. of a subject while increasing the inner pressure of a cuff attached to the subject.

SUMMARY OF INVENTION

Technical Problem

Figure 6A:
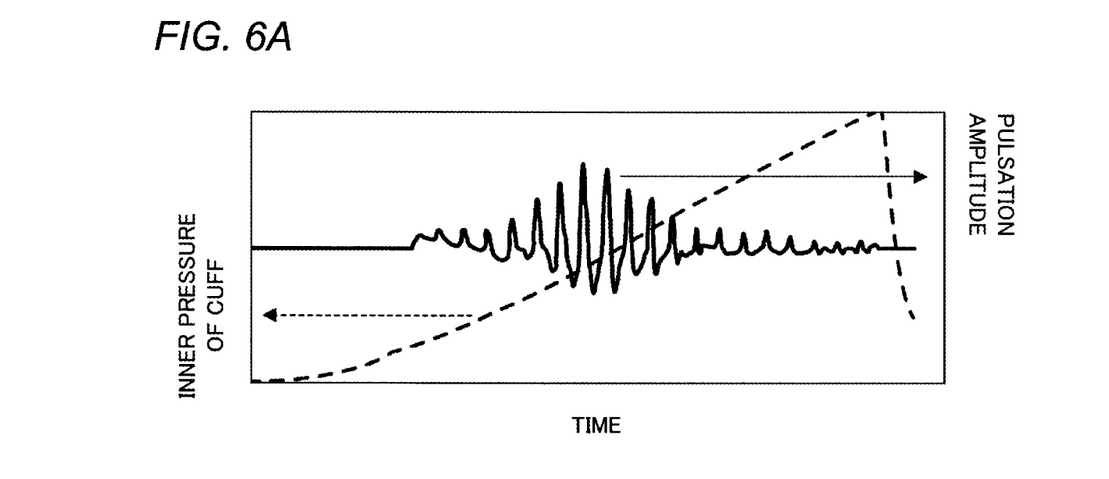
FIG. 6A illustrates an operation example of an inflation blood pressure measuring apparatus.

FIG. 6A shows a common operation of the above type of inflation blood pressure measuring apparatus. In FIG. 6A, the dashed line represents the inner pressure of the cuff and the solid line represents the amplitude of a pulsation signal generated by a pressure sensor or the like. The amplitude of the pulsation signal corresponds to the magnitude of vibration that is caused by beating of an artery being pressed by the cuff. How the amplitude of the pulsation signal varies is monitored while the cuff pressure is being increased, and blood pressures (systolic blood pressure, diastolic blood pressure, etc.) are determined on the basis of magnitudes of amplitudes. Thus, to determine blood pressures correctly, it is necessary to detect a pulsation signal accurately.

Figure 6B:
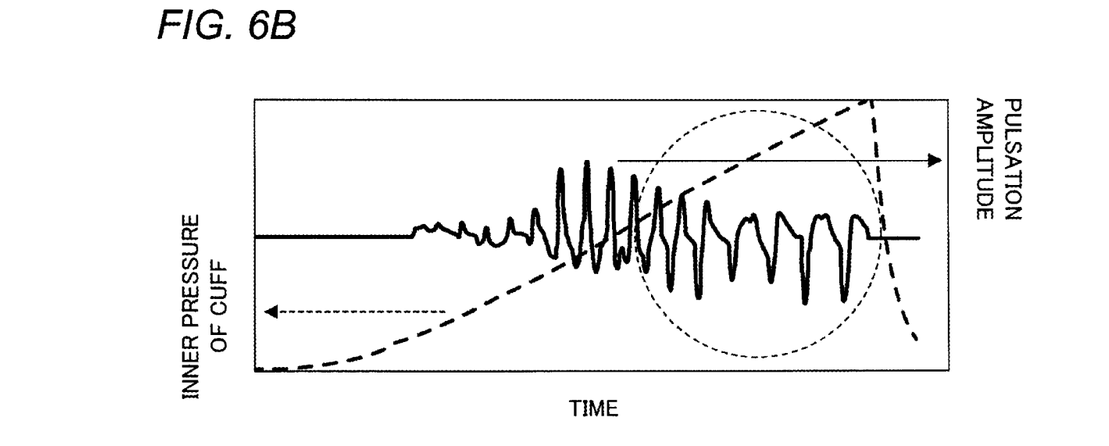
FIG. 6B illustrates an operation example of an inflation blood pressure measuring apparatus.

An event may occur such that, for example, the position of the cuff attached to a subject is deviated or the cuff becomes loose during inflation of the cuff. FIG. 6B shows how the inner pressure of the cuff and the pulsation signal vary over time in a case that such an event has occurred. If, for example, the cuff position is deviated or the cuff becomes loose, periodical noise is superimposed on the pulsation signal. In the interval that is circled in FIG. 6B, periodical noise due to deviation of the cuff position, cuff loosening, or the like is superimposed on the pulsation signal. Also being periodic, this noise is hard to discriminate from the intrinsic pulsation signal. This may cause a problem that blood pressures cannot be determined correctly because amplitudes of the intrinsic pulsation signal cannot be detected accurately.

An object of the present disclosure is to enable detection of an inappropriate attachment state of a cuff in order to avoid a situation that a blood pressure is measured with the cuff being in the inappropriate attachment state.

Solution to Problem

According to one aspect of the disclosure, there is provided a blood pressure measuring apparatus for measuring a blood pressure of a subject using a cuff attached to the subject, comprising:
a processor; and
a memory configured to store instructions that is readable by the processor, wherein the blood pressure measuring apparatus is configured to, as the instructions are executed by the processor:
acquire pulsation information of the subject that is to be used to determine the blood pressure, while increasing an inner pressure of the cuff;
acquire first-order differential values of the pulsation information; and
detect an inappropriate attachment state of the cuff on the basis of at least one of:
a local minimal value of the first-order differential values;
a first variation of the first-order differential values including the local minimal value in a unit time;
a first relationship between a local maximal value and the local minimal value of the first-order differential values; and
a second relationship between the first variation and a second variation of the first-order differential values including the local maximal value in a unit time.

A pressure variation due to beating of an artery acts so as to increase the inner pressure of the cuff. This variation is reflected so as to increase the first-order differential value. On the other hand, noise due to positional deviation or loosening of the cuff acts so as to decrease the inner pressure of the cuff. This variation is reflected so as to decrease the first-order differential value. Thus, in the case where the cuff is not attached appropriately, the first-order differential values have a remarkable profile in an area of the local minimal value thereof than an area of the local maximal value thereof.

Accordingly, with the above configuration, an inappropriate attachment state of the cuff can be detected using the simple processing of differentiating once the pulsation information that is acquired in processing of inflating the cuff. A situation can thereby be avoided that a blood pressure is measured with the cuff being in an inappropriate attachment state.

According to one aspect of the disclosure, there is provided a blood pressure measuring apparatus for measuring a blood pressure of a subject using a cuff attached to the subject, comprising:
a processor; and
a memory configured to store instructions that is readable by the processor,
wherein the blood pressure measuring apparatus is configured to, as the instructions are executed by the processor:
acquire pulsation information of the subject that is to be used to determine the blood pressure, while increasing an inner pressure of the cuff;
acquire second-order differential values of the pulsation information; and
detect an inappropriate attachment state of the cuff on the basis of at least one of:
a local minimal value of the second-order differential values;
a first variation of the second-order differential values including the local minimal value in a unit time;
a first relationship between a local maximal value and the local minimal value of the second-order differential values; and
a second relationship between the first variation and a second variation of the second-order differential values including the local maximal value in a unit time.

Since features relating to an inappropriate attachment state of the cuff may be reflected in the second-order differential values more remarkably than the first-order differential values, the use of the second-order differential values makes it possible to detect the inappropriate attachment state of the cuff more correctly. Thus, it becomes possible to avoid more reliably a situation that a blood pressure is measured with the cuff being in an inappropriate attachment state.

DESCRIPTION OF EMBODIMENTS

Figure 1:
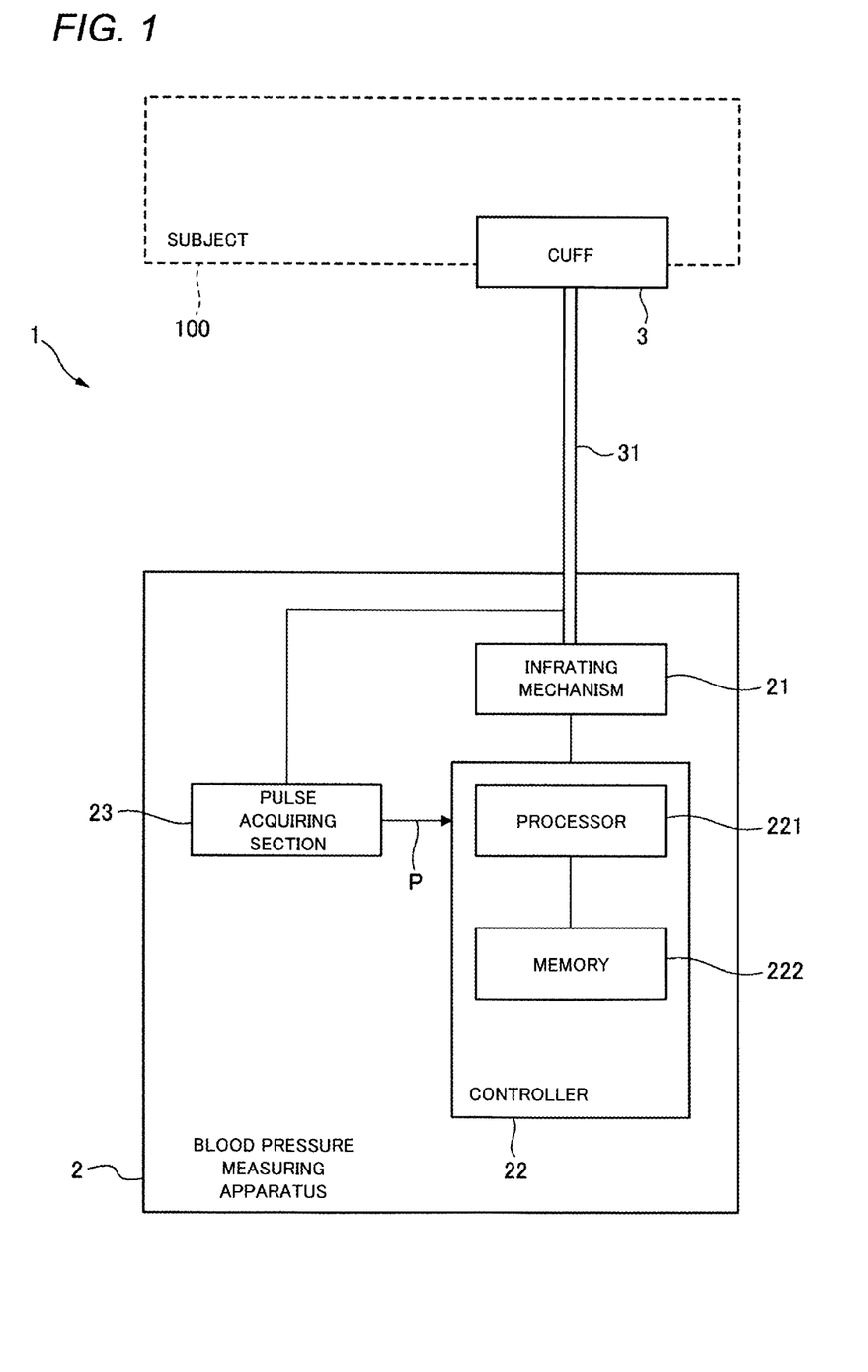
FIG. 1 illustrates a functional configuration of a blood pressure measuring system according to one embodiment.

Embodiments will be described below in detail with reference to the accompanying drawings. FIG. 1 shows a functional configuration of a blood pressure measuring system 1 according to one embodiment. The blood pressure measuring system 1 comprises a blood pressure measuring apparatus 2 and a cuff 3.

The blood pressure measuring apparatus 2 is an apparatus for measuring a blood pressure of a subject 100 using the cuff 3 attached to the subject 100, and comprises an inflating mechanism 21, a controller 22, and a pulse acquiring section 23.

The inflating mechanism 21, which is connected to the cuff 3 by a tube 31, has a pump function and a valve function. The pump function serves to increase the inner pressure of the cuff 3 by sending air to it through the tube 31. The valve function serves to connect or disconnect the tube 31 to or from the external air. The inner pressure of the cuff 3 lowers if the tube 31 is connected to the external air in a state that the pump function is not in operation.

The controller 22 comprises processor 221 and a memory 222. As the processor 221, a CPU and an MPU can be exemplified. The processor 221 may include a plurality of cores. Examples of the memory 222 include a ROM and a RAM. The ROM may be stored with various computer-readable instructions. The processor 221 may designates at least a part of the instructions stored in the ROM that is to be executed on the RAM. The processor 221 may cooperate with the RAM in order to execute operations as described below in detail.

The pulse acquiring section 23 is implemented by a sensor for acquiring pulsation information of the subject 100. The pulse acquiring section 23 is configured to output a pulsation signal P corresponding to beating of an artery of the subject 100. More specifically, the pulse acquiring section 23 generates a pulsation signal P by causing an output signal of a pressure sensor for detecting an inner pressure of the cuff 3 to pass through a highpass filter. Thus, it can be said that the pulsation signal P is a high-frequency signal indicating a temporal variation of the inner pressure of the cuff 3. The pulsation signal P that is output from the pulse acquiring section 23 is input to the controller 22.

Figure 2:
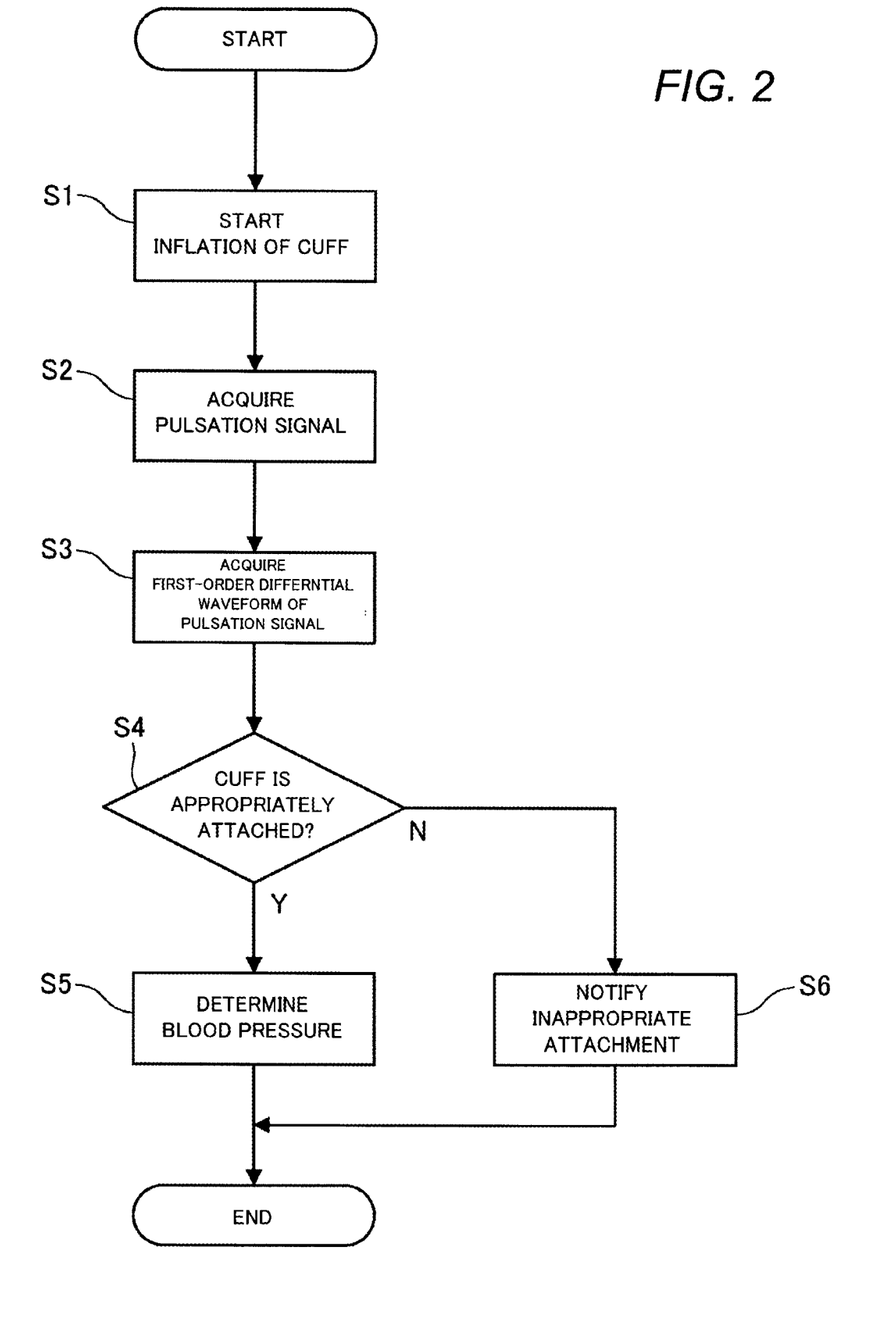
FIG. 2 illustrates an operation example of a blood pressure measuring apparatus shown in FIG. 1.

The blood pressure measuring apparatus 2 is configured to execute processing shown in FIG. 2 as instructions stored in the memory 222 are executed by the processor 221 in the controller 22.

First, at step S1, the blood pressure measuring apparatus 2 activates the pump function of the inflating mechanism 21 and thereby increases the inner pressure of the cuff 3 at a prescribed inflation rate.

At step S2, the blood pressure measuring apparatus 2 acquires a pulsation signal P of the subject 100 via the pulse acquiring section 23. The pulsation signal P is an example of pulsation information. Alternatively, acquisition of a pulse rate may be started before the inflating operation of the inflating mechanism 21.

At step S3, the blood pressure measuring apparatus 2 generates a first-order differential signal PD1 by performing first-order differentiation on the pulsation signal P acquired from the pulse acquiring section 23. That is, the controller 22 acquires first-order differential values of the pulsation information of the subject 100.

Figure 3A:
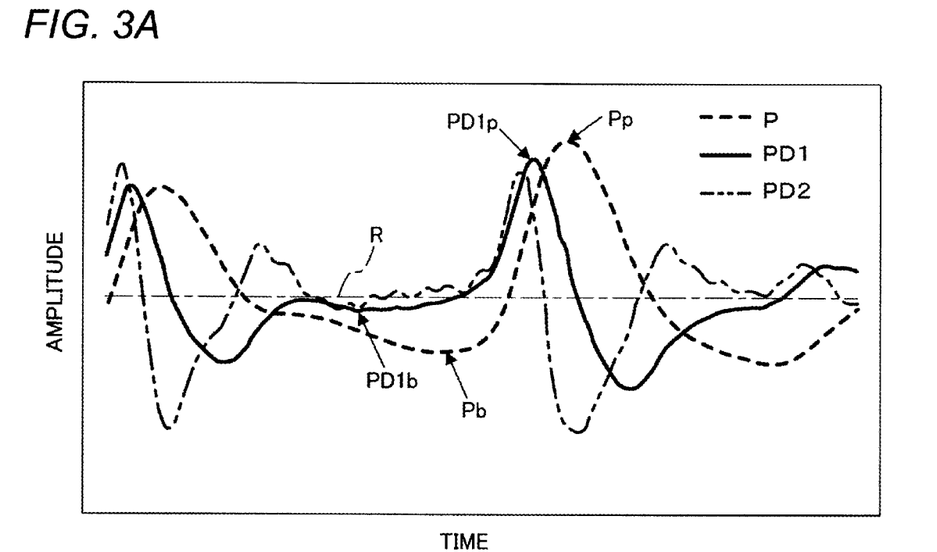
FIG. 3A is a diagram for explaining operations of the blood pressure measuring apparatus shown in FIG. 1.
Figure 3B:
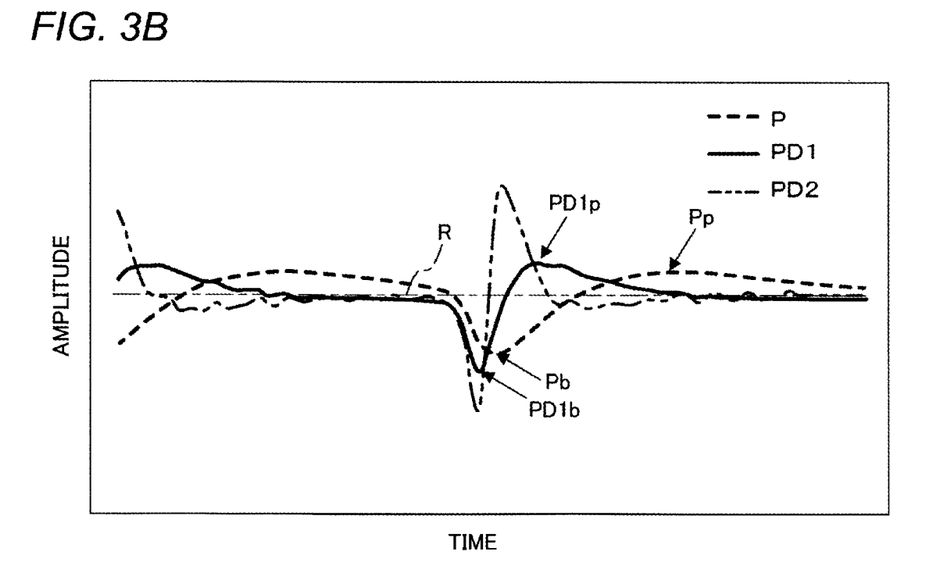
FIG. 3B is a diagram for explaining operations of the blood pressure measuring apparatus shown in FIG. 1.

FIG. 3A shows waveforms of a pulsation signal P and a first-order differential signal PD1 in a case that the cuff 3 is attached appropriately. FIG. 3B shows waveforms of a pulsation signal P and a first-order differential signal PD1 in a case that the position of the cuff 3 is deviated or the cuff 3 is loose (i.e., the cuff 3 is not attached appropriately). In each of FIGS. 3A and 3B, the horizontal chain line indicates the zero level of the first-order differential signal PD1.

A pressure variation due to beating of an artery acts so as to increase the inner pressure of the cuff 3. This variation is reflected in the first-order differential signal PD1 in such a direction as to increase its amplitude. On the other hand, noise due to positional deviation or loosening of the cuff 3 acts so as to decrease the inner pressure of the cuff 3. This variation is reflected in the first-order differential signal PD1 in such a direction as to decrease its amplitude. Thus, as shown in FIG. 3B, in the case where the cuff 3 is not attached appropriately, the first-order differential signal PD1 becomes such that a waveform element that is convex downward is dominant over or more remarkable than a waveform element that is convex upward.

At step S4 (see FIG. 2), the blood pressure measuring apparatus 2 judges whether the cuff 3 is attached appropriately on the basis of the above fact relating to the first-order differential signal PD1.

In a first example, the blood pressure measuring apparatus 2 makes a judgment on the basis of a bottom value PD1$b$ of the first-order differential signal PD1 in a certain cycle (a prescribed period of the pulsation signal P). The bottom value PD1$b$ is an example of a local minimal value of first-order differential values. More specifically, the blood pressure measuring apparatus 2 judges that the cuff 3 is not attached appropriately if a bottom value PD1$b$ that appears immediately before a peak value PD1$p$ in the first-order differential signal PD1 in a certain cycle is smaller than a prescribed value. An example of the prescribed value is a value that is smaller than the amplitude reference level R shown in FIG. 3 by 1 mmHg.

In a second example, the blood pressure measuring apparatus 2 makes a judgment on the basis of the sharpness of a waveform portion including a bottom value PD1$b$ of the first-order differential signal PD1 in a certain cycle. More specifically, the blood pressure measuring apparatus 2 makes a judgment on the basis of an amplitude variation in a unit time containing a bottom value PD1$b$ that appears immediately before a peak value PD1$p$ in the first-order differential signal PD1 in a certain cycle. The amplitude variation in the unit time containing the bottom value PD1$b$ is an example of a first variation.

Figure 4:
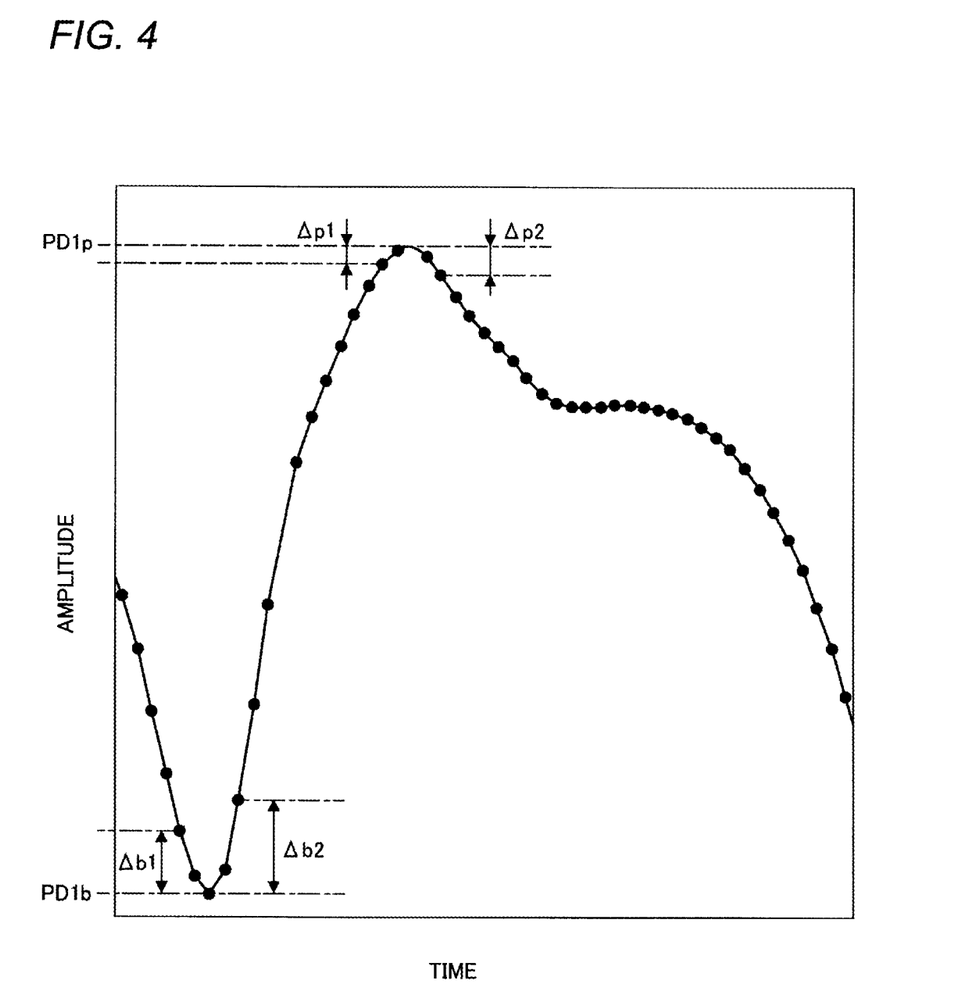
FIG. 4 is a diagram for explaining operations of the blood pressure measuring apparatus shown in FIG. 1.

As shown in FIG. 4, the first-order differential signal PD1 consists of plural first-order differential values that respectively correspond to plural measured values constituting the pulsation signal P. Since the plural measured values are acquired at a fixed time interval, the plural measured values are also acquired at the fixed time interval. For example, the above-mentioned unit time may be defined as a time taken to acquire five first-order differential values that are the bottom value PD1$b$, two first-order differential values preceding the bottom value PD1$b$, and two first-order differential values following the bottom value PD1$b$. In this case, the above-mentioned "amplitude variation in the unit time containing the bottom value PD1$b$" can be defined as the sum of variations delta-b1 and delta-b2 shown in FIG. 4. The blood pressure measuring apparatus 2 judges that the cuff 3 is not attached appropriately if the sum of the variations delta-b1 and delta-b2 is larger than a prescribed value.

In a third example, the blood pressure measuring apparatus 2 makes a judgment on the basis of a relationship between a bottom value PD1$b$ and a peak value PD1$p$ of the first-order differential signal PD1 in a certain cycle. More specifically, the blood pressure measuring apparatus 2 judges that the cuff 3 is not attached appropriately if the absolute value of a bottom value PD1$b$ that appears immediately before a peak value PD1$p$ in the first-order differential signal PD1 in a certain cycle is larger than the absolute value of the peak value PD1$p$. The peak value PD1$p$ is an example of a local maximal value of first-order differential values.

In a fourth example, the blood pressure measuring apparatus 2 makes a judgment on the basis of a relationship between the sharpness of a waveform portion including a bottom value PD1$b$ of the first-order differential signal PD1 in a certain cycle and the sharpness of a waveform portion including a peak value PD1$p$ of the first-order differential signal PD1 in the certain cycle. More specifically, the blood pressure measuring apparatus 2 judges that the cuff 3 is not attached appropriately if a waveform portion including a bottom value PD1$b$ of the first-order differential signal PD1 in a certain cycle is sharper than a waveform portion including a peak value PD1$p$ of the first-order differential signal PD1 in the certain cycle.

The method for determining the sharpness of a waveform portion including a bottom value PD1$b$ is the same as described above. The sharpness of a waveform portion including a peak value PD1$p$ may be determined as an amplitude variation of the first-order differential signal PD1 in a unit time containing the peak value PD1$p$. The amplitude variation in the unit time containing the peak value PD1$p$ is an example of a second variation. The unit time may be defined as a time taken to acquire five first-order differential values that are the peak value PD1$p$, two first-order differential values preceding the peak value PD1$p$, and two first-order differential values following the peak value PD1$p$. In this case, the above-mentioned "amplitude variation in the unit time containing the peak value PD1$p$" can be defined as the sum of variations delta-p1 and delta-p2 shown in FIG. 4. The blood pressure measuring apparatus 2 judges that the cuff 3 is not attached appropriately if the sum of the variations delta-b1 and delta-b2 is larger than the sum of the variations delta-p1 and delta-p2.

The blood pressure measuring apparatus 2 may employ either only one or plural ones of the above four judgment criteria. In the latter case, the blood pressure measuring apparatus 2 may judge that the cuff 3 is not attached appropriately if at least one of the criteria employed is satisfied.

As shown in FIG. 2, if judging that the cuff 3 is attached appropriately (S4: Y), at step S5 the blood pressure measuring apparatus 2 determines a blood pressure of the subject 100 on the basis of the pulsation signal P.

On the other hand, if judging that the cuff 3 is not attached appropriately (S4: N), at step S6 the blood pressure measuring apparatus 2 notifies the fact with at least one of a visual notification, an auditory notification, and a tactile notification.

With the above configuration, an inappropriate attachment state of the cuff 3 can be detected using the simple processing of differentiating once a pulsation signal P that is acquired in processing of inflating the cuff 3. A situation can thereby be avoided that a blood pressure is measured with the cuff 3 being in an inappropriate attachment state.

Determination itself of a blood pressure may be done at step S5 parallel with the notification. In this case, a judgment as to whether a determined blood pressure is appropriate is left to a health care professional who should also take the notification into consideration.

Alternatively, the blood pressure measuring apparatus 2 may be configured to refrain from determining a blood pressure on the basis of the pulsation signal P if that a prescribed criterion is satisfied in making the above judgment, the prescribed criterion (the satisfaction of which means a high probability of inappropriate attachment of the cuff 3) being at least one of the following requirements 1 and 2:

Requirement 1: The ratio of the absolute value of a bottom value PD1$b$ that appears immediately before a peak value PD1$p$ in the first-order differential signal PD1 in a certain cycle to the absolute value of the peak value PD1$p$ is larger than or equal to a prescribed ratio. For example, the prescribed ratio is 1.5. This requirement is an example of a first relationship.

Requirement 2: The ratio of an amplitude variation indicating the sharpness of a waveform portion including a bottom value PD1$b$ that appears immediately before a peak value PD1$p$ in the first-order differential signal PD1 in a certain cycle to an amplitude variation indicating the sharpness of a waveform portion including the peak value PD1$p$ is larger than or equal to a first prescribed ratio and the ratio of the absolute value of the bottom value PD1$b$ to that of the peak value PD1$p$ is larger than or equal to a second prescribed ratio. For example, the first prescribed ratio is 2 and the second prescribed ratio is 0.5. This requirement is an example of a second relationship.

With the above configuration, it is made easier to avoid a situation that a blood pressure is measured with the cuff 3 being in an inappropriate attachment state.

In each of the above examples of the processing of judging whether the cuff 3 is in an inappropriate attachment state, a judgment is made on the basis of a peak value PD1$p$ and a bottom value PD1$b$ of the first-order differential signal PD1 of the pulsation signal P in a certain cycle as well as amplitude variations of the first-order differential signal PD1 including the peak value PD1$p$ and the bottom value PD1$b$. Each of the peak value PD1$p$ and the bottom value PD1$b$ may be an average of plural values acquired in a prescribed time period (a time period corresponding to five pulsations of the subject 100, for example).

With the above configuration, it is possible to increase the correctness, in a statistical sense, of the processing of judging whether the cuff 3 is in an inappropriate attachment state. That is, it becomes easier to avoid a situation that the cuff 3 is judged in an inappropriate attachment state as a result of an event that the above parameters of the first-order differential signal PD1 satisfy the criterion by chance. Thus, it becomes easier to avoid a situation that a blood pressure is measured with the cuff 3 being in an inappropriate attachment state.

FIGS. 3A and 3B also show a waveform of a second-order differential signal PD2 of the pulsation signal P. In each of FIGS. 3A and 3B, the horizontal reference level R also coincides with the zero level of the second-order differential signal PD2. It is found from comparison between the first-order differential signal PD1 and the second-order differential signal PD2 that the second-order differential signal PD2 exhibits, in a more emphasized manner, the tendency that a waveform element that is convex downward is more remarkable in the case that the cuff 3 is not attached appropriately. It is also found that the second-order differential signal PD2 exhibits, in a more emphasized manner, the tendency that a maximum value is reached earlier in the case that the cuff 3 is not attached appropriately. It is noted that a case having only one of these two tendencies may occur.

Based on the above discussion, the blood pressure measuring apparatus 2 may acquire a second-order differential signal PD2 in addition to or in place of a first-order differential signal PD1 by differentiating the pulsation signal P twice. The second-order differential signal PD2 is an example of the second-order differential values of the pulsation information. A criterion for judging whether the cuff 3 is in an inappropriate attachment state may be such as to correspond to at least one of the above-mentioned four criteria.

The blood pressure measuring apparatus 2 may be configured to execute the judgment step using the second-order differential signal PD2 if it is judged that the judgment as to whether the cuff 3 is in an inappropriate attachment state cannot be made properly as long as only the first-order differential signal PD1 is used. Alternatively, the process may always proceed to acquisition of a second-order differential signal PD2 and judgment using the acquired second-order differential signal PD2.

Figure 5:
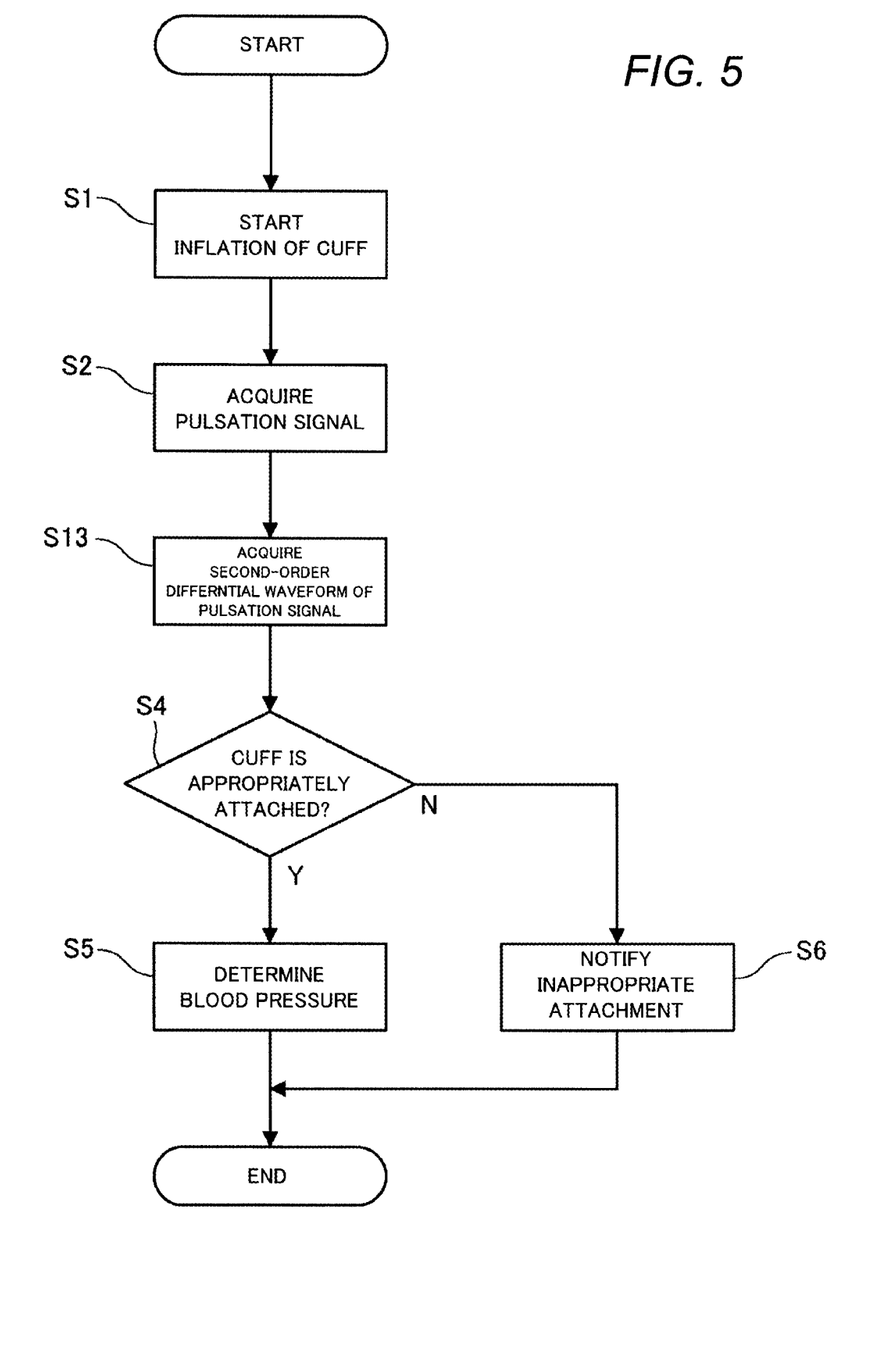
FIG. 5 illustrates an operation example of a blood pressure measuring apparatus shown in FIG. 1.

FIG. 5 is a flowchart of such processing of the blood pressure measuring apparatus 2. Steps that are substantially the same as those in the processing of FIG. 2 are designated with the same reference symbols as the latter. Step S13 is a step of acquiring a second-order differential signal PD2. Alternatively, the processing may always proceed to acquisition of a second-order differential signal PD2 and comparison between a result of a judgment using the first-order differential signal PD1 and a result of a judgment using the second-order differential signal PD2.

Since features relating to an inappropriate attachment state of the cuff 3 may be reflected in the second-order differential signal PD2 more remarkably than the first-order differential signal PD1, the use of the second-order differential signal PD2 makes it possible to detect an inappropriate attachment state of the cuff 3 more correctly. Thus, it becomes possible to avoid more reliably a situation that a blood pressure is measured with the cuff 3 being in an inappropriate attachment state.

The above-described embodiment is just an example for facilitating understanding of the present disclosure, and the configuration of the embodiment can be modified or improved as appropriate without departing from the fundamental concept of the present disclosure.

The inflating mechanism 21 and the controller 22 of the blood pressure measuring apparatus 2 need not always be disposed in a common casing. At least part of the functions of the controller 22 may be implemented by a computing device of a computer that is connected to the blood pressure measuring apparatus 2.

The pulse acquiring section 23 need not always be disposed in the blood pressure measuring apparatus 2, and may be configured to be attachable to the body of a subject.

The present application is based on Japanese Patent Application No. 2017-065003 filed on Mar. 29, 2017, the entire contents of which are hereby incorporated by reference.

What is claimed is:

1. A blood pressure measuring apparatus for measuring a blood pressure of a subject using a cuff attached to the subject, comprising:
a processor; and
a memory configured to store instructions that is readable by the processor, wherein the blood pressure measuring apparatus is configured to, as the instructions are executed by the processor:
acquire pulsation information of the subject that is to be used to determine the blood pressure, while increasing an inner pressure of the cuff;
acquire second-order differential values of the pulsation information; and
detect an inappropriate attachment state of the cuff using at least one of:
a local minimal value of the second-order differential values;
a first variation of the second-order differential values including the local minimal value in a unit time;
a first relationship between a local maximal value and the local minimal value of the second-order differential values; and
a second relationship between the first variation and a second variation of the second-order differential values including the local maximal value in a unit time,
wherein the blood pressure measuring apparatus is configured to refrain from determining the blood pressure if the inappropriate attachment state of the cuff is detected.

2. The blood pressure measuring apparatus according to claim 1, wherein at least one of the local minimal value, the first variation, the local maximal value, and the second variation is calculated as a mean value of plural values acquired in a prescribed time period.

3. The blood pressure measuring apparatus according to claim 1, wherein the first relationship is a comparison between an absolute value of the local maximal value and an absolute value of the local minimal value of the second-order differential values.

4. The blood pressure measuring apparatus according to claim 1, wherein the first variation is calculated using the local minimal value of the second-order differential values, a second-order differential value preceding the local minimal value, and a second-order differential value following the local minimal value.

5. The blood pressure measuring apparatus according to claim 1, wherein the second variation is calculated using the local maximum value of the second-order differential values, a second-order differential value preceding the local maximum value, and a second-order differential value following the local maximum value.

6. A blood pressure measuring apparatus for measuring a blood pressure of a subject using a cuff attached to the subject, comprising:
a processor; and
a memory configured to store instructions that is readable by the processor, wherein the blood pressure measuring apparatus is configured to, as the instructions are executed by the processor:

acquire pulsation information of the subject that is to be used to determine the blood pressure, while increasing an inner pressure of the cuff;
acquire second-order differential values of the pulsation information;
detect an inappropriate attachment state of the cuff using at least one of:
  a local minimal value of the second-order differential values;
  a first variation of the second-order differential values including the local minimal value in a unit time;
  a first relationship between a local maximal value and the local minimal value of the second-order differential values; and
  a second relationship between the first variation and a second variation of the second-order differential values including the local maximal value in a unit time; and
notify, based on detection of the inappropriate attachment state of the cuff, a fact indicative of the detection of the inappropriate attachment state of the cuff with at least one of a visual notification, an auditory notification, or a tactile notification.

* * * * *